(12) United States Patent
Singer

(10) Patent No.: US 8,685,742 B2
(45) Date of Patent: Apr. 1, 2014

(54) APPARATUS AND METHOD FOR THE MORE EFFICIENT ISOLATION OF NUCLEIC ACIDS

(75) Inventor: Thorsten Singer, Solingen (DE)

(73) Assignee: Qiagen GmbH, Hilden (DE)

( * ) Notice: Subject to any disclaimer, the term of this patent is extended or adjusted under 35 U.S.C. 154(b) by 291 days.

(21) Appl. No.: 11/572,076

(22) PCT Filed: Jul. 15, 2005

(86) PCT No.: PCT/EP2005/007726
§ 371 (c)(1),
(2), (4) Date: Aug. 16, 2007

(87) PCT Pub. No.: WO2006/008085
PCT Pub. Date: Jan. 26, 2006

(65) Prior Publication Data
US 2008/0039619 A1    Feb. 14, 2008

(30) Foreign Application Priority Data
Jul. 15, 2004    (DE) .......................... 10 2004 034 474

(51) Int. Cl.
*B01D 37/00* (2006.01)
(52) U.S. Cl.
USPC ................................ 436/117; 436/8; 435/6.1
(58) Field of Classification Search
None
See application file for complete search history.

(56) References Cited

U.S. PATENT DOCUMENTS

| | | | |
|---|---|---|---|
| 4,647,380 A | | 3/1987 | Dasgupta |
| 5,234,809 A | | 8/1993 | Boom et al. |
| 5,578,459 A | * | 11/1996 | Gordon et al. ................... 135/29 |
| 5,674,997 A | * | 10/1997 | Woodard et al. ............. 536/25.4 |
| 6,218,531 B1 | * | 4/2001 | Ekenberg ................... 536/25.41 |
| 6,277,648 B1 | * | 8/2001 | Colpan ......................... 436/177 |
| 6,699,987 B2 | * | 3/2004 | Hillebrand et al. .......... 536/25.4 |
| 7,531,308 B2 | * | 5/2009 | Ray et al. ........................... 435/5 |
| 2003/0003455 A1 | * | 1/2003 | Rundell et al. .................... 435/6 |
| 2008/0039619 A1 | | 2/2008 | Singer |

FOREIGN PATENT DOCUMENTS

| | | |
|---|---|---|
| DE | 4139664 | 6/1993 |
| EP | 0 461 477 A1 | 12/1991 |
| EP | 1321176 | 6/2003 |
| JP | 2002-209580 A | 7/2002 |
| WO | 93/11221 A1 | 6/1993 |
| WO | 95/14533 A1 | 6/1995 |
| WO | 00/34463 A1 | 6/2000 |

OTHER PUBLICATIONS

Ahern et al. The Scientist, vol. 9, Issue 15, p. 20., 1995.*
Vogelstein & Gillespie, (1979). Preparative and analytical purification of DNA from agarose. Proc. Natl Acad. Sci., USA, 76, 615-619.
Marko, M.A., Chipperfield, R. and Birnbiom, H.G., (1982). A procedure ofr the large-sclae isolation of highly purified plasmid DNA using alkaline extraction and binding to glass powder. Anal. Biochem., 121, (1982), 382-387.

(Continued)

*Primary Examiner* — Sally Merkling
(74) *Attorney, Agent, or Firm* — Seed IP Law Group PLLC

(57) ABSTRACT

The present invention relates to an apparatus and a method for the more efficient cleaning of nucleic acids, and to a kit for carrying out this method.

19 Claims, 4 Drawing Sheets

(56) References Cited

OTHER PUBLICATIONS

Sambrook, J., Fritsch, E.F., Maniatis, T. (1989). Molecular Cloning: A Laboratory Manual. 2nd Ed. E3-E4; E10-E1 1.
Whatman Webseite: http://www.whatman.com/products.aspx?pid=13.
F&J Specialty Products, Inc: the Nucleus of Quality Air Monitoring Programs; Filter Paper for Air Sampling and Other Uses; http://www.fjspecialty.com/filtpap.htm.
Third Party Observation for Application No. EP20050761702; Title: Device and Method for More Efficient Isolation of Nucleic Acids; Publication Number: EP1771242; Dated April 4, 2013.
Genomic DNA Isolation, Smarter Nucleic Acid Sample Preparation, http://www.invitek.de/products_and_service/products/single_tube_kits/ (2 pages) (Nov. 27, 2012).
Instruction for Invisorb® Plasmid Midi Kit or Invisorb® Plasmid Maxi Kit, (30 pages) (2011).
Kwon, Kideok D., "Interactions of biopolymers with silica surfaces: Force measurements and electronic structure calculation studies," *Geochimica et Cosmochimica Acta*, 70:3803-3819 (2006).
Mouse ScFv Module/Recombinant Phage Antibody System—Instructions, *Amersham Biosciences*, (2 pages) (1995).
QIAGEN Plasmid Purification Handbook, Third Edition, (52 pages) (Nov. 2005).

\* cited by examiner

Preparation times (min)

| Product 1 | Product 2 | Product 3 | Product 4 |
|---|---|---|---|
| 45 | 100 | 70 | 20 |

Yields (µg)

|  | Product 1 | Product 2 | Product 3 | Product 4 |
|---|---|---|---|---|
| Test 1 | 126 | 201 | 246 | 304 |
| Test 2 | 115 | 239 | 154 | 246 |
| Mean value | 121 | 220 | 200 | 275 |

Elution volumes (µl)

| Product 1 | Product 2 | Product 3 | Product 4 |
|---|---|---|---|
| 480 | 720 | 970 | 100 |
| 460 | 800 | 970 | 100 |

Fig. 5

Preparation times (min)

| Invitek | According to the invention |
|---|---|
| 50 | 20 |

Fig. 6

Yields (µg)

| Test | Invitek | According to the invention |
|---|---|---|
| 1 | 1084 | 1395 |
| 2 | 900 | 1168 |
| Mean value | 992 | 1282 |

Fig. 7

Elution volumes

| Invitek | According to the invention |
|---|---|
| 670 | 200 |
| 660 | 200 |

| Quantity of DNA used | 10 µg | 50 µg | 100 µg | 250 µg |
|---|---|---|---|---|
| 1 | 6,8 | 20 | 70 | 233 |
| 2 | 6,0 | 29 | 73 | 190 |
| Mean value | 6,4 | 29 | 71,5 | 211 |

APPARATUS AND METHOD FOR THE MORE EFFICIENT ISOLATION OF NUCLEIC ACIDS

CROSS REFERENCE TO RELATED APPLICATIONS

This application is a national stage 35 USC §371 application of International Application No. PCT/EP05/007726 filed Jul. 15, 2005 which claims priority to German Application No. 102004034474.4 filed Jul. 15, 2004.

BACKGROUND OF THE INVENTION

1. Field of the Invention

The present invention relates to an apparatus and a method using the apparatus for the more efficient cleaning of nucleic acids, and to a kit for carrying out this method.

2. Description of Related Art

As is known from the state of the art, the isolation of nucleic acids from complex biological starting materials is carried out under strongly denaturising and reducing conditions. The starting materials containing the nucleic acids are partially solubilised using protein-degrading enzymes, and the escaping nucleic acid fractions are cleaned by means of a phenol/chloroform extraction step. The nucleic acids can then subsequently be obtained from the aqueous phase by means of dialysis or ethanol precipitation (J. Sambrock, E. F. Fritsch and T. Maniatis, 1989, Cold Spring Harbor, "Molecular Cloning").

The methods for the isolation of nucleic acids known from the state of the art have the disadvantage, however, that they are time-consuming and necessitate a considerable outlay on apparatus. In addition, such methods can be shown as being hazardous to health due to the chemicals used, such as phenol and chloroform.

In order to avoid the harmful and expensive phenol/chloroform extraction of nucleic acids combined with an additional reduction in the time required for carrying out experiments, various alternative methods for the isolation of nucleic acids from different biological starting materials have been developed in the past.

These include methods, which are based on a method described for the first time by Vogelstein and Gillespie (Proc. Natl. Acad. Sci. USA, 1979, 76, 615-619) for the preparative and analytical cleaning of DNA fragments from agarose gels. This method combines the dissolving of the agarose containing the DNA band to be isolated in a saturated solution of a chaotropic salt (NaJ) with a subsequent bonding of the DNA to glass particles.

The DNA fixed to the glass particles is subsequently washed with a washing solution (20 mM Tris HCl [pH 7.2], 200 mM NaCl; 2 mM EDTA; 50% v/v ethanol) and then eluted from the carrier particles. This method has been frequently modified in the course of time and is presently used for different methods of extraction and cleaning of nucleic acids of widely differing origin.

A large number of reagent systems (kits) currently exist, mainly for the cleaning of DNA fragments from agarose gels and also for the isolation of plasma DNA from bacterial lysates, which is associated with an additional isolation of longer-chain nucleic acids (genomic DNA, cellular RNA) from blood, tissue and also cell cultures.

These commercially available kits are based on the sufficiently well-known principle of bonding nucleic acids to mineral carriers under the presence of solutions of different chaotropic salts, wherein the carrier materials, for example, contain suspensions of finely ground glass powder (e.g. Glasmilk, BIO 101, La Jolla, Calif.), diatomic earths (Sigma) or even silica gels (Qiagen, DE 41 39 664 A1).

In addition, various methods for the isolation of nucleic acids have been used in the state of the art in order to bond the starting materials to a DNA-bonding solid phase by means of a chaotropic buffer (U.S. Pat. No. 5,234,809). Here, the chaotropic buffers are used both for the lysis of the starting material and also for the bonding of the nucleic acids to the solid phase.

With this method, nucleic acids from small sample quantities can be used, especially when used for the isolation of viral nucleic acids. The incubation of the starting material with the chaotropic buffer and with the DNA-bonding solid phase has the disadvantage that the cell decomposition, which is to be realised by the chaotropic buffer, cannot be used for all materials, and also can only be used extremely inefficiently and with considerable time expenditure particularly for larger quantities of starting materials. Therefore, additional mechanical homogenisation methods are often used (e.g. in the isolation of DNA from tissue samples). Varyingly high concentrations of different chaotropic buffers must be used for different objectives, and therefore—by nature—cannot be applied universally.

In order to simplify the possibly difficult lysis of the starting material, a series of commercially available products can be used for isolating the nucleic acids, which however are then no longer based on an easily manageable so-called "single tube" method.

The chaotropic salts necessary for the subsequent bonding of the nucleic acids (e.g. to centrifugation membranes) must be added to the lysis preparation in a special method step when the lysing is complete. On the other hand, these chaotropic salts cannot be part of the lysis buffer however, as the protein-destroying function is inherent to the chaotropic substances and these would also destroy the proteolytic enzymes necessary for efficient lysis.

The methods described above and known from the state of the art for isolating nucleic acids using chaotropic salts have become established worldwide and are freely applied in their millions using commercially available products.

According to the principle of starting-material lysis, in a simple execution, the nucleic acids are bonded to the solid phase of a glass or silica membrane, which is located on a carrier substance in a centrifuge column. The bonded nucleic acids are subsequently eluted with a buffer of lower ion strength.

The physical-chemical principle of the bonding of nucleic acids to mineral carriers in the presence of chaotropic salts has been explained in professional circles. It has been postulated that the bonding of nucleic acids to the surfaces of mineral carriers is based on a breaking down of superimposed structures of the aqueous environment, by means of which the nucleic acids adsorb on the surface of mineral materials, in particular of glass or silica particles.

When the concentrations of the chaotropic salts are high, the reaction proceeds almost quantitatively. For this reason, a buffer composition with high ion strengths of chaotropic salts is important for bonding nucleic acids to a nucleic-acid-bonding solid phase.

For the bonding of nucleic acids to the respective carrier surfaces, the buffer solution contains at least one chaotropic salt as its main component. Under certain circumstances, this even includes the lysis buffer or, in systems that use proteolytic enzymes, a necessary bonding buffer, which is added to the starting material after lysis is complete.

The Hofmeister series for salting out negatively charged, neutral or basic protein solutions forms the basis for chaotropic salts. Chaotropic salts are characterised in that they denature proteins, increase the solubility of unpolar substances in water, and destroy hydrophobic interactions. These characteristics also effect the destruction of superimposed structures of the aqueous environment with buffer systems of chaotropic salts, in order to promote the bonding of the nucleic acids to selected solid phases.

The best-known examples of chaotropic salts for isolating nucleic acids include sodium perchlorate, sodium iodide, potassium iodide, guanidinium-iso-thiocyanate and guanidinium hydrochloride. However, they are cost-intensive and also, to some extent, toxic or irritant.

A method for the isolation of DNA from tissue and cell lines is described in the state of the art, in which the cells are dispersed in a buffer containing guanidinium hydrochloride, and precipitated in ethanol (Analytical Biochemistry 162, 1987, 463). On the one hand, this method is susceptible to contamination, but on the other, a usable nucleic acid product can be isolated within a few hours.

In addition, a method for the isolation of nucleic acids using antichaotropic substances is known from the state of the art. Here, an improved isolation of nucleic acids can likewise be achieved by the addition of antichaotropic salts in a lysis/bonding buffer system. Antichaotropic components include ammonium, caesium, sodium and/or potassium salts, preferably ammonium chloride. When using lysis/bonding buffer systems without the chaotropic salt constituents, nucleic acids, particularly genomic DNA, can be bonded to a mineral carrier material and also eluted under the usual reaction conditions.

Furthermore, it has been found that at least the same quantitative and qualitative results are achieved with lysis/bonding buffers, the main components of which are ammonium salts, for example, instead of chaotropic salts, in extractions of genomic DNA from starting materials of different complexity (e.g. blood, tissue, plants) using the previously common (alternative) reaction components and carrier materials and with the same reaction process.

It has thus been observed that with salts, which do not denaturise but stabilise proteins, and do not degrade but reinforce hydrophobic interactions, it is also equally possible to isolate nucleic acids from complex starting materials.

Low concentrations of salts (less than 1 M) are adequate for bonding nucleic acids to solid carriers. In certain applications, concentrations less than 0.5 M are preferred, higher ion concentrations being necessary for the quantitative isolation of nucleic acids from larger quantities of starting materials.

These lysis/bonding buffer systems known from the state of the art, which have at least one antichaotropic salt component, are therefore capable of bonding nucleic acids to solid phases, which have a negatively charged surface, or which contain surfaces, which are capable of exhibiting a negative charge potential.

The reaction sequence of the isolation of nucleic acids from a complex starting material is realised by carrying out the lysis of the starting material, bonding the nucleic acids, washing the bonded nucleic acids, and eluting the nucleic acids in a reaction vessel, and requires at least one centrifugation step.

The methods of isolating plasmid DNA with the usual midi and maxi systems previously known from the state of the art are, however, only scaled-up mini preparations whose columns have either been increased to a larger diameter or supplemented by very many membrane layers in order to achieve the required capacity. Systems of this kind are currently supplied by manufacturers such as Stratagene or Sigma for example.

The glass fibre membranes employed here work almost exclusively using chaotropic salts for selective bonding to the surface of the membrane.

The main disadvantage is the complex handling (many centrifugation steps with large floor-mounted centrifuges). Added to this is a relatively large elution volume combined with a large dead volume due to the large internal surfaces and the resulting larger membrane volumes.

As a result of this surface area, which is necessary for increasing the capacity, the processing of larger preparations with an apparatus based on the mini format while maintaining a chaotropic bonding chemistry has not previously been possible.

On the other hand, plasmid isolation based on an alcoholic bonding chemistry has previously only been possible using the Invisorb® Plasmid Kits produced by the company Invitek (Berlin). But even in these kits, columns are used, which are not suitable for preparations on a midi/maxi scale due to their dimensions. The disadvantages already described therefore apply to these.

SUMMARY OF THE INVENTION

The object of the present invention henceforth consists in providing an apparatus and a method, which allow DNA plasmid isolations to be carried out on a large scale (in so-called maxi or midi preparations), and at the same time avoid time-consuming centrifugation steps using large floor-mounted centrifuges.

According to the invention, the problem is solved by the use of a so-called mini spin column, which in itself is known from the state of the art, but which has a special membrane. According to the invention, the membrane allows a rapid percolation of the lysate/alcohol mixture on the one hand, and, on the other, a sufficiently large bonding/filter capacity is guaranteed. As an option—depending on the requirements—an additional filter layer can be placed over the membrane in order to prevent premature clogging.

BRIEF DESCRIPTION OF THE FIGURES

Further particulars of the present invention are explained in more detail with reference to attached drawings (FIGS. 1 to 10) and the exemplary embodiments described below.

In the drawings:

FIG. 5: shows elution volumes (in μl) of 4 column preparations—with column material from the companies Invitek (Product 1), SIGMA (Product 2) and Stratagene (Product 3) and the apparatus according to the invention (Product 4)—while changing the column format from the midi preparation to the mini preparation FIG. 6: shows preparation times (in min) of 2 different column preparations—with column material from the company Invitek and the apparatus according to the invention—during the cleaning of nucleic acids before changing the maxi preparation to the mini preparation.

FIG. 7: shows DNA yields (in μg) of 2 different column preparations—with column material from the company Invitek and the apparatus according to the invention—for cleaning nucleic acids during the reduction of the column format from the maxi preparation to the mini preparation.

DETAILED DESCRIPTION OF A PREFERRED EMBODIMENT

Figure 1A:
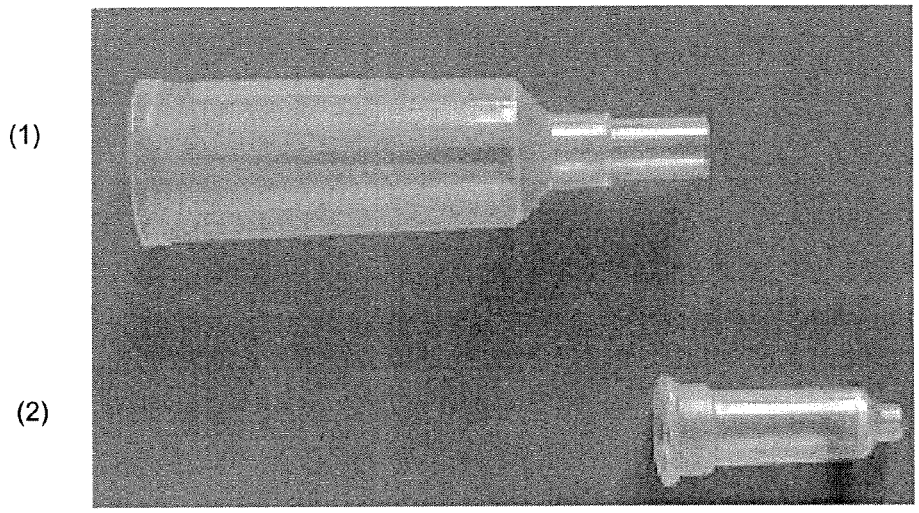
FIG. 1a and FIG. 1b: show a column combination consisting of an open hollow body (1) with an inlet opening and an outlet opening, and a further hollow body (2) with an inlet opening and an outlet opening, with a containing filter layer in the lumen.
Figure 1B:
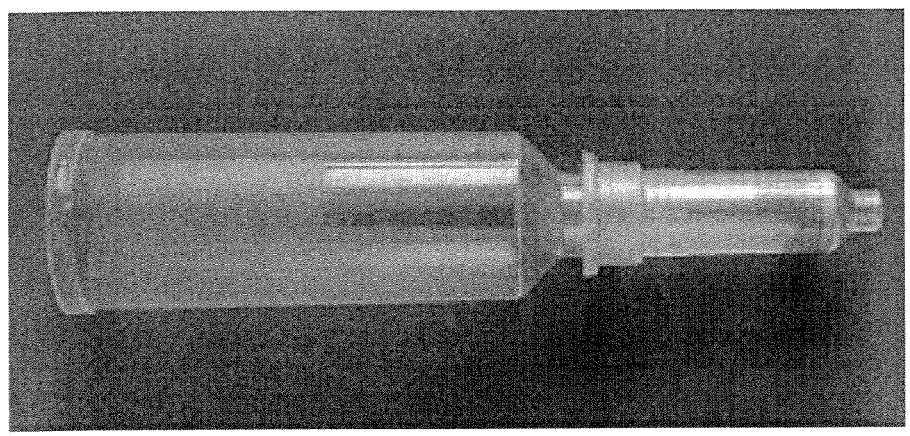

According to the present invention, the use of the membranes described above for the method according to the invention has a decisive influence on the bonding of DNA to the silica membrane, which preferably can be located in a hollow body of a column suitable for chromatography, in particular for ion exchanger chromatography. It must be ensured here that the membrane has a suitable pore size, which, on the one hand, can hold back the DNA, and, on the other, also enable good percolation without clogging when filtering larger quantities. Furthermore, the internal surface of the chromatography column should be coated with a chromatographic material suitable for ion exchange.

According to the invention, so-called GF/A, GF/B and GF/D membranes from Whatman are used. These are membranes, which are made up of micro glass fibres and which are used mainly for filtration purposes (for example for cleaning water). Here, there is a reducing percolation speed in the order GF/D (2.7 μm)>>GF/A (1.6 μm)>GF/B (1 μm).

The bonding of nucleic acids to the surface of mineral carriers in the presence of chaotropic salts requires membrane pore sizes of ca. 1 μm in order to achieve acceptable yields, which increases the percolation times for large volumes to such an extent that the bonding step would be really time-consuming.

Surprisingly, it has been found that membranes, which have a pore size in the range of 2-4 μm, bond DNA with a high yield at a high percolation speed if an alternative (non-chaotropic) bonding chemistry is used.

This can avoid the disadvantage of the long percolation time. Therefore, according to the invention, an aliphatic alcohol with 1 to 5 carbon atoms—preferably ethanol or isopropanol—is used for the bonding of nucleic acids, which allows the use of larger membrane pores, and thus decisively reduces the percolation time and, associated with this, the preparation time.

Carrying out the present invention also makes it possible to elute the nucleic acids with a column in mini format with a small amount of buffer.

Here, the elution volume obtained using the relatively small membranes compared with those used in the midi and maxi format described above was identical to the amount of buffer used. The advantage of the constant elution volume of this so-called "quick preparation method" consists in the fact that the actual volume does not have to be determined separately in order to determine the total yield. In addition, the DNA solution is highly concentrated and can be easily diluted if necessary. In contrast with this, a very diluted solution, which is obtained using state-of-the-art methods, would have to be concentrated with considerably more effort.

To accommodate the larger volumes for the midi/maxi scale, the spin column is fitted with an appropriate extender tube. The apparatus according to the invention for cleaning nucleic acids therefore includes a column combination consisting of:

a. an open hollow body (1) with an inlet opening and an outlet opening, which is arranged on a further b. open hollow body (2) with an inlet opening and an outlet opening, with one or more membranes attached therein.

The column/extender combination is then placed on a vacuum chamber (e.g. the QIAvac® 6S produced by the company QIAGEN, 40724 Hilden) and the sample drawn through the membrane by means of vacuum. The extender tube is subsequently discarded and the mini spin column is processed further in accordance with known mini preparation methods (e.g. using QIAprep®, produced by the company QIAGEN, 40724 Hilden).

The great advantage of the proposed method according to the invention and the apparatus used with it consists in the short processing time for cleaning nucleic acids and in dispensing with impractical, complex centrifugation steps. Added to this are low elution and dead volumes and the associated high final DNA concentrations.

EXAMPLE 1

Protocol for the Isolation of Plasmid DNA from *E. coli* on a So-called Midi Scale Protocol for the Isolation of Plasmid DNA from *E. coli*:
25 ml *E. coli* DH5α—culture with the plasmid pCMVβ (DH5α/pCMVβ, from the company BD Biosciences).

(1) Resuspend bacteria pellet in 2 ml resuspension buffer (3 min)
(2) Add 2 ml lysis buffer and mix carefully. Lyse for ca. 3 min
(3) Add 2 ml neutralisation buffer, mix by inverting (1 min)
(4) Place the raw lysate over a filter column containing silica (QIAfilter QIAGEN), incubate for 3 min at room temperature and press the raw lysate through the column material.
(5) Place 10 ml extension tube on the spin column and position on a QIAvac® (QIAGEN).
(6) Add 2.5 ml isopropanol to the lysate, mix well and place on the column.
(7) Suck the mixture through the column material for 2 min with the help of vacuum.
(8) Discard the extension tube
(9) Place the spin column containing the silica membranes on a collection tube (collection vessel).
(10) Wash by adding 750 μl buffer PE, (QIAGEN, commercially available alcohol wash buffer) and centrifuge for 1 min at 14,000 rpm.

(11) Centrifuge once more for 1 min at 14,000 rpm to remove buffer residues.
(12) Switch the spin column to a 1.5 ml Eppendorf tube.
(13) For elution, pipette 200 µl of an elution buffer (EB), e.g. the commercially available elution buffer TE, onto the membrane, allow to stand for 1 min and centrifuge (1 min at 14,000 rpm).

Here, the items (4), (7) and (10)-(13) listed in the protocol for the isolation of plasmid DNA lead to significantly faster isolation of plasmid DNA compared with the systems known from the state of the art.

With regard to the example given above, reference preparations with the following silica-based products were carried out:
1) Invitek Invisorb Plasmid Midi Kit (Invitek),
2) SIGMA GeneElute EF Midi Kit (SIGMA-ALDRICH),
3) Stratagene Strataprep EF Midi (Stratagene),
4) the apparatus according to the invention For better compatibility with the two other systems, in preparations (2) and (3) the protocol variant was carried out without the optional endotoxin removal step specified in the protocol.

Moreover, the Invitek Invisorb Plasmid Midi Kit (1) and the method used with the apparatus according to the invention (4) are based on a non-chaotropic silica chemistry. On the other hand, the SIGMA (2) and Stratagene (3) kits are based on a conventional bonding by means of chaotropic salts.

Figures 2, 3, 4:
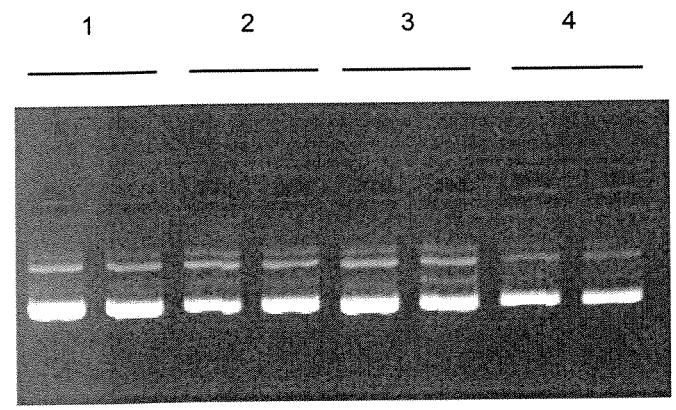
FIG. 2: shows preparation times (in min) of 4 different column preparations—with column material from the companies Invitek (Product 1), SIGMA (Product 2) and Stratagene (Product 3) and the apparatus according to the invention (Product 4)—according to Example 1 during the cleaning of nucleic acids.
FIG. 3: shows DNA yields (in µg) of 4 different column preparations—with column material from the companies Invitek (Product 1), SIGMA (Product 2) and Stratagene (Product 3) and the apparatus according to the invention (Product 4)—according to Example 1 during the cleaning of nucleic acids.
FIG. 4: shows an agarose gel with the bands of 4 column preparations—with column material from the companies Invitek (Product 1), SIGMA (Product 2) and Stratagene (Product 3) and the apparatus according to the invention (Product 4).

FIG. 2 shows the preparation times in minutes (min) of 4 different column preparations. Here, with 20 min, the apparatus according to the invention enables a clearly shorter preparation time to be achieved for the isolation of nucleic acids than the methods from Invitek, SIGMA and Stratagene, which are known from the state of the art.

In addition, the DNA yields in micrograms (µg) of the 4 column preparations are shown in FIG. 3, wherein the yield of 275 µg of the apparatus according to the invention or of the method carried out with this apparatus (the "quick preparation midi") is clearly higher than that of the Invitek, SIGMA or Stratagene preparations.

FIG. 4 shows without a doubt that the preparations carried out in accordance with the invention are of identical quality to the samples isolated with the methods known from the state of the art.

The elution volumes in microliters (µl) of the 4 column preparations are compared in FIG. 5. These make it clear that the columns used in mini format according to the invention can be eluted with a smaller amount of buffer. The small membrane results in no dead volume, so that the elution volume obtained is identical to the volume of buffer solution used.

The very low and constant elution volume of the "quick preparation method" provides great advantages for determining the total yield and for the following applications, as the DNA solution is highly concentrated and can be easily diluted if necessary. In contrast with this, a diluted solution would have to be concentrated with considerably more effort.

EXAMPLE 2

Isolation of Plasmid DNA from *E. coli* on a So-called Maxi Scale

Protocol for the Isolation of Plasmid DNA from *E. coli*
100 ml *E. coli* DH5α—culture with the plasmid pCMVβ (DH5α/pCMVβ, from the company BD Biosciences)
(1) Resuspend bacteria pellet in 5 ml resuspension buffer (3 min)
(2) Add 5 ml lysis buffer and mix carefully. Lyse for ca. 3 min.
(3) Add 5 ml neutralisation buffer, mix by inverting (1 min).
(4) Place the raw lysate over a filter column containing silica (QIAfilter QIAGEN), incubate for 3 min at room temperature and press the raw lysate through the column material.
(5) Place 20 ml extension tube on the spin column and position on a QIAvac.
(6) Add 7 ml isopropanol to the lysate, mix well and place on the column.
(7) Suck the mixture through the column material for 2 min with the help of vacuum.
(8) Discard the extension tube.
(9) Place the spin column containing the silica membranes on a collection tube (collection vessel).
(10) Wash by adding 750 µl PE of a commercially available wash buffer and centrifuge for 1 min at 14,000 rpm.
(11) Centrifuge once more for 1 min at 14,000 rpm to remove the buffer residues.
(12) Switch the spin column to a 1.5 ml Eppendorf tube.
(13) For elution, pipette 200 µl of an elution buffer (EB), e.g. the commercially available elution buffer TE, onto the membrane, allow to stand for 1 min and centrifuge (1 min at 14,000 rpm).

With the example given above, reference preparations with the following silica-based products were carried out:
1) Invitek Invisorb Plasmid Maxi Kit (Invitek)
2) the apparatus according to the invention The apparatus according to the invention and the Invitek product are both based on a non-chaotropic silica chemistry.

FIG. 6 shows the preparation times (in min) of 2 different column preparations. Here, (as in Example 1), with 20 min, the apparatus according to the invention shows a likewise clearly shorter preparation time for the isolation of nucleic acids compared with the Invitek preparation based on the same chemistry.

FIG. 7 shows (as in Example 1) the DNA yields (in µg) of the 2 column preparations.

Figures 8, 9, 10:
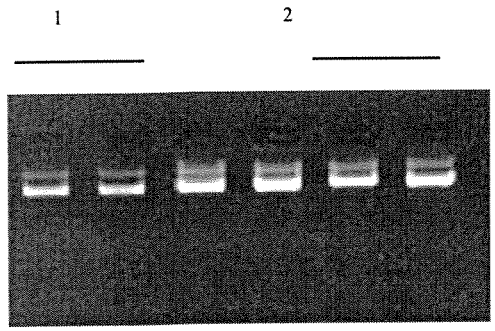
FIG. 8: shows an agarose gel with the bands of 2 column preparations—with column material from the company Invitek (1) and the apparatus according to the invention (2).
FIG. 9: shows elution volumes (in μl) of 2 different column preparations—with column material from the company Invitek and the apparatus according to the invention—during the change of the column format from the maxi preparation to the mini preparation.
FIG. 10: shows the effect of the GF/D membrane with a pore size of 2.7 μm on the DNA yields (in μg).

By referring to the bands in the agarose gel in FIG. 8, it could be shown that an identical quality of the two reference preparations had been achieved, while the yield of 1282 µg when using the apparatus according to the invention is however clearly higher than that of the comparison preparation (Invitek).

These yields cannot be achieved with chaotropic bonding chemistry, as only bonding points on the inner surface of the membrane can be used in this case, which rules out the use of a mini spin column and the method according to the invention.

The elution volumes (in µl) of two column preparations are compared in FIG. 9, from which it can be clearly seen that, with the mini format column used in accordance with the method according to the invention, DNA can also be eluted with a smaller amount of buffer. The small integral membrane results in virtually no dead volume, so that the elution volume obtained is practically identical to the volume of buffer used.

EXAMPLE 3

Effect of the GF/D Membrane on the Apparatus According to the Invention for the Isolation of Nucleic Acids when Changing the Reduced Column Preparation from Midi Scale to Mini Scale A synthetic lysate was manufactured from resuspension buffer, lysis buffer and neutralisation buffer. 6 ml of this "lysate" in each case were then mixed with different quantities of plasmid DNA (10 μg-250 μg), isopropanol was added and sucked through the column of the apparatus according to the invention, which contained 2 layers of a GF/D membrane (from the company Whatman) in each case.

FIG. 10 shows the DNA yields (in μg) of the column preparation after adding increasing amounts of plasmid DNA (10 μg-250 μg). It was shown that with increasing amounts of plasmid DNA (10 μg-250 μg) the achievable DNA yield rose to 211 μg.

The percolation speeds lie between 10-35 ml/min, depending on the applied vacuum (ca. 600-20 mbar).

Additional investigations show that a high yield can be achieved at large percolation speed when using membranes, which have a nominal average pore size of 2-5 μm.

EXAMPLE 4

Percolation Speeds Using Filter Matting on a Maxi Scale

This experiment shows the effect of a filter mat (35 g/m$^2$) on the percolation speed of the apparatus according to the invention.

Protocol for the Isolation of Plasmid DNA from *E. coli*:

100 ml *E. coli* DH5α—culture with the plasmid pCMVβ (DH5α/pCMVβ, from the company BD Biosciences).

The *E. coli* culture was lysed following the preparation steps in accordance with the maxi protocol described in Example 2, the lysate clarified by filtration, and mixed with isopropanol.

The lysate/isopropanol mixture was then pressed through the column at 200 mbar. The preparation column was fitted with a filter mat (35 g/m$^2$).

A percolation speed of 7.2 ml/min was observed with the apparatus according to the invention and the filter mat used.

Considerably higher volumes of lysate could be processed due to this improved resistance to clogging, as a result of which the method can also be used on a larger scale.

The invention claimed is:

1. A method for cleaning nucleic acids comprising:
    a) introducing a nucleic acid-containing mixture prepared in a midi or maxi scale into an apparatus comprising a column combination comprising:
        i) an open hollow body with an inlet opening and an outlet opening, and
        ii) a mini spin column with an inlet opening, an outlet opening, and a membrane, wherein the membrane is contained in the mini spin column and comprises a glass fiber membrane with a pore size in a range of 2-4 μm,
        wherein the open hollow body is removably arranged on the mini spin column,
    b) bonding the nucleic acids to the membrane in the presence of an aliphatic alcohol with 1 to 5 carbon atoms, but in the absence of a chaotropic agent, and
    c) eluting the nucleic acids from the membrane in the mini spin column with an elution buffer.

2. A kit for carrying out the method according to claim 1, comprising:
    a) an open hollow body with an inlet opening and an outlet opening;
    b) a mini spin column with an inlet opening, an outlet opening, and a membrane, wherein the membrane is contained in the mini spin column and comprises a glass fiber membrane with a pore size in a range of 2-4 μm, wherein the mini spin column is adapted so that the open hollow body may be removably arranged on the mini spin column;
    c) a reagent for bonding a nucleic acid to the membrane comprising an aliphatic alcohol with 1 to 5 carbon atoms, but no chaotropic agents; and
    d) optionally further means suitable for cleaning nucleic acids.

3. The kit according to claim 2, further comprising one or more of cell culture medium, resuspension buffer, lysis buffer, neutralisation buffer, wash buffer, and elution buffer.

4. The method of claim 1 wherein the membrane comprises a GF/D membrane.

5. The method of claim 1, wherein the inner surface of the mini spin column is coated with a chromatographic material suitable for ion exchange.

6. The method of claim 1, wherein said aliphatic alcohol comprises ethanol.

7. The method of claim 4, wherein said aliphatic alcohol comprises ethanol.

8. The method of claim 5, wherein said aliphatic alcohol comprises ethanol.

9. The method of claim 1, wherein said aliphatic alcohol comprises isopropanol.

10. The method of claim 4, wherein said aliphatic alcohol comprises isopropanol.

11. The method of claim 5, wherein said aliphatic alcohol comprises isopropanol.

12. The method of claim 1, wherein said apparatus further comprises a filter placed over said membrane.

13. The method of claim 4, wherein said apparatus further comprises a filter placed over said membrane.

14. The method of claim 5, wherein said apparatus further comprises a filter placed over said membrane.

15. The method of claim 1, wherein the nucleic acid-containing mixture comprises 10 μg to 250 μg plasmid DNA.

16. The method of claim 1, wherein the amount of the nucleic acids eluted from the membrane is in a range of 6 μg to 1395 μg.

17. The method of claim 16, wherein the amount of the nucleic acids eluted from the membrane is in a range of 29 μg to 1395 μg.

18. The method of claim 1, wherein the amount of the nucleic acids eluted from the membrane is in a range of 70 μg to 1395 μg.

19. The method of claim 18, wherein the amount of the nucleic acids eluted from the membrane is in a range of 70 μg to 233 μg.

* * * * *

UNITED STATES PATENT AND TRADEMARK OFFICE
CERTIFICATE OF CORRECTION

| | | |
|---|---|---|
| PATENT NO. | : 8,685,742 B2 | |
| APPLICATION NO. | : 11/572076 | |
| DATED | : April 1, 2014 | |
| INVENTOR(S) | : Thorsten Singer | |

It is certified that error appears in the above-identified patent and that said Letters Patent is hereby corrected as shown below:

On the Title Page
Item (56):
"Sambrook, J., Fritsch, E.F., Maniatis, T. (1989). Molecular Cloning: A Laboratory Manual. 2$^{nd}$ Ed. E3-E4; E10-E1 1." should read, --Sambrook, J., Fritsch, E.F., Maniatis, T. (1989). Molecular Cloning: A Laboratory Manual. 2$^{nd}$ Ed. E3-E4; E10-E11.--.

In the Claims
Column 10, Line 51:
"18. The method of claim 1, wherein the amount of the" should read, --18. The method of claim 17, wherein the amount of the--.

Signed and Sealed this
Sixteenth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,685,742 B2
APPLICATION NO. : 11/572076
DATED : April 1, 2014
INVENTOR(S) : Thorsten Singer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 632 days.

Signed and Sealed this
Thirtieth Day of May, 2017

Michelle K. Lee
*Director of the United States Patent and Trademark Office*